US012365654B2

United States Patent
Pradhan et al.

(10) Patent No.: US 12,365,654 B2
(45) Date of Patent: Jul. 22, 2025

(54) PROCESS FOR THE PREPARATION OF HIGHLY PURE VALSARTAN

(71) Applicant: HARMAN FINOCHEM LIMITED, Mumbai (IN)

(72) Inventors: Nitin Sharadchandra Pradhan, Thane (IN); Vijay Trimbak Kadam, Aurangabad (IN); Vishalkumar Rajendrakumar Shah, Aravalli (IN); Pankaj Shrawan Chaudhari, Jalgaon (IN); Harpreet Singh Minhas, Mumbai (IN); Gurpreet Singh Minhas, Mumbai (IN)

(73) Assignee: HARMAN FINOCHEM LIMITED, Mumbai (IN)

( * ) Notice: Subject to any disclaimer, the term of this patent is extended or adjusted under 35 U.S.C. 154(b) by 661 days.

(21) Appl. No.: 17/782,048

(22) PCT Filed: Nov. 28, 2020

(86) PCT No.: PCT/IN2020/050990
§ 371 (c)(1),
(2) Date: Jun. 2, 2022

(87) PCT Pub. No.: WO2021/111464
PCT Pub. Date: Jun. 10, 2021

(65) Prior Publication Data
US 2023/0057675 A1  Feb. 23, 2023

(30) Foreign Application Priority Data
Dec. 2, 2019 (IN) .............................. 201921049418

(51) Int. Cl.
C07D 257/04   (2006.01)
G01N 30/02    (2006.01)

(52) U.S. Cl.
CPC ........... *C07D 257/04* (2013.01); *G01N 30/02* (2013.01); *G01N 2030/027* (2013.01)

(58) Field of Classification Search
CPC ... C07D 257/04; G01N 30/02; G01N 2030/02
See application file for complete search history.

(56) References Cited

U.S. PATENT DOCUMENTS

| 5,260,325 A | 11/1993 | Markwalder et al. |
| 5,399,578 A | 3/1995 | Buhlmayer et al. |
| 5,965,592 A | 10/1999 | Buhlmayer et al. |
| 6,271,375 B1 | 8/2001 | Villa et al. |

FOREIGN PATENT DOCUMENTS

| EP | 2167477 A2 | 3/2010 |
| WO | 1997030036 A1 | 8/1997 |
| WO | 1999067231 A1 | 12/1999 |
| WO | 2001082858 A2 | 11/2001 |
| WO | 2002006253 A1 | 1/2002 |
| WO | 2018040065 A1 | 3/2018 |

OTHER PUBLICATIONS

Peter Buhlmayer, et al., Bioorganic & Medicinal Chemistry Letters, vol. 4 (1), pp. 29-34, 1994.
"Abiotic and Biotic Mechanisms Controlling in situ Remediation of NDMA" SERDP project ER-1421, https://apps.dtic.mil/sti/pdfs/ADA606789.pdf 5.1.1 on p. 5.1.
"Scientific and technical assessment report on Nistrosamines" Nov. 1977, Publication No. 6007701, https://hepis.epa.gov/Exe/ZyPURL.cgi?Dockey=9101AUJ9.txt., p. 198, section 8.1.3.5.
International Search Report for PCT/IN2020/050990 mailed Feb. 25, 2021.
Written Opinion for PCT/IN2020/050990 mailed Feb. 25, 2021.

*Primary Examiner* — Kamal A Saeed
(74) *Attorney, Agent, or Firm* — Kramer & Amado, P.C.

(57) ABSTRACT

Disclosed herein is a process for the preparation and purification of Valsartan. The process according to the invention is capable of removing the toxic nitroamine impurities and providing substantially pure Valsartan.

19 Claims, No Drawings

PROCESS FOR THE PREPARATION OF HIGHLY PURE VALSARTAN

FIELD OF THE INVENTION:

The present invention relates to a process for the preparation of highly pure Valsartan which is free from toxic nitroso amine impurities.

BACKGROUND OF THE INVENTION:

Valsartan is chemically known as N-(1-oxopentyl)-N-[[2'-(1H-tetrazol-5-yl) [1,1'-biphenyl]-4-yl]methyl]-L-valine (formula-1). Valsartan is a nonpeptide, orally active, and specific angiotensin II receptor blocker acting on the AT1 receptor subtype. Angiotensin II antagonists are useful as therapeutic for cardiovascular complaints such as hypertension, heart failure, stroke.

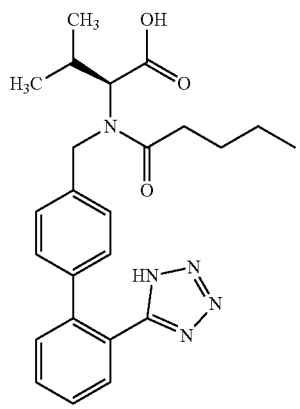

Formula-1

VALSARTAN

Valsartan and its pharmaceutically acceptable salts are disclosed in U.S. Pat. No. 5,399,578. U.S.'578 discloses the process for preparing Valsartan which comprises the reaction of L-valine methyl ester hydrochloride with 4-bromo methyl-2'-cyanobiphenyl to produce 4-[(2'-cyanobiphenyl-4-yl)methyl]-(L)-valine methyl ester which reacts with valeryl chloride to give N-[(2'-cyanobiphenyl-4-yl)methyl]-N-valeryl-(L)-valine methyl ester which reacts with tributyltin azide to give Valsartan methyl ester which is then hydrolyzed under alkaline condition to give finally Valsartan. The synthesis reported in US'578 is shown in scheme 1.

Scheme-1

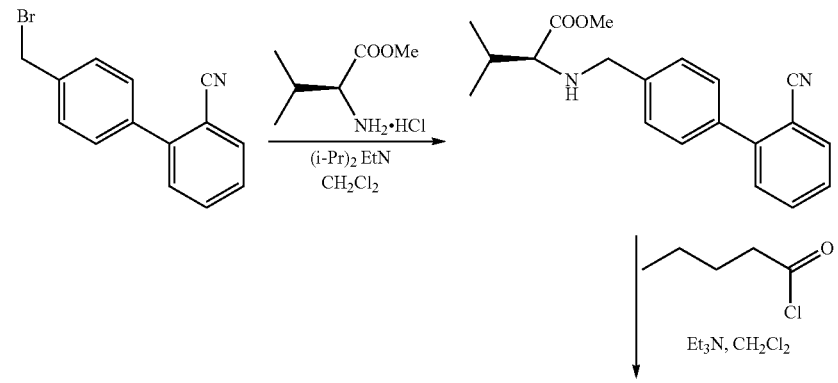

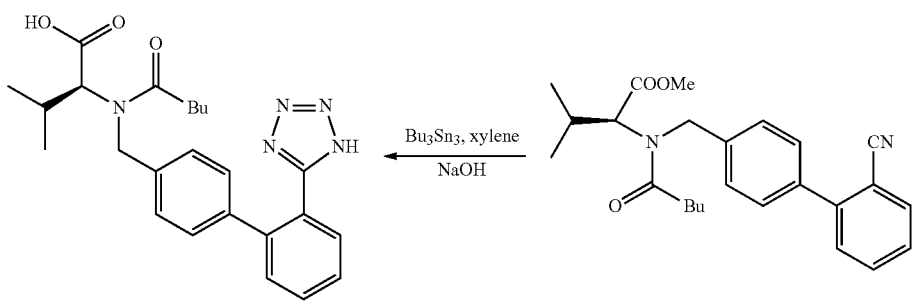

Valsartan and/or its intermediates are disclosed in various references including U.S. Pat. Nos. 5,965,592, 5,260,325, 6,271,375, WO 02/006253, WO 01/082858, WO 99/67231, WO 97/30036 and Peter Buhlmayer, et. al., Bioorganic & Medicinal Chemistry Letters, Vol. 4 (1), pp 29-34, 1994.

The major concern about the process for the preparation of Valsartan as reported in the above prior arts is the presence of genotoxic and carcinogenic impurities such as nitroso amine impurities in the end product. These impurities are highly toxic in nature. Therefore, there is an urgent and pressing need to develop a process for the preparation of Valsartan, wherein such process is capable of eliminating all those harmful nitrosamine impurities and to obtain a substantially pure Valsartan which complies with stringent regulatory requirements of health agencies i.e. USFDA and EMEA. These toxic nitroso amine impurities are generated due to side reactions during the synthetic process for the production of valsartan or due to use of certain organic solvents.

The structures of toxic nitroso amine impurities are depicted below;

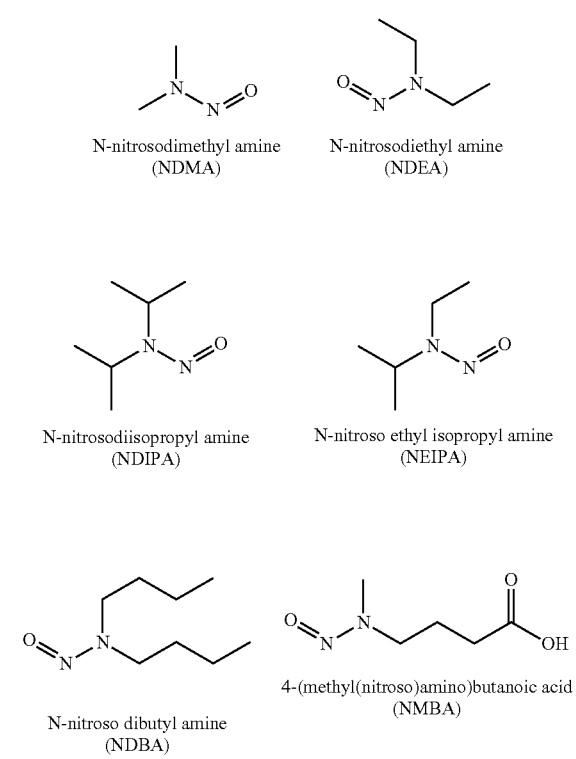

Thus, there remains a need in the art for a process for the purification of Valsartan which is substantially free from N-nitrosodimethyl amine (NDMA), N-nitrosodiethyl amine (NDEA), N-nitrosodiisopropyl amine (NDIPA), N-nitroso ethyl isopropyl amine (NEIPA), N-nitroso dibutyl amine (NDBA) and 4-(methyl(nitroso)amino)butanoic acid (NMBA) impurities.

Interestingly, the present inventors have found a process for the preparation of highly pure Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino)butanoic acid (NMBA) impurities.

The present inventors have also found a process for the purification of Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino)butanoic acid (NMBA) impurities.

The present inventors have surprisingly found that Sodium dithionite commonly known as Sodium hydrosulfite or hydrose plays an important role in the removal of these toxic impurities from crude Valsaran.

SUMMARY OF THE INVENTION:

The present invention provides a process for the preparation of Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino)butanoic acid (NMBA) impurities which process comprises; treating the crude valsartan with sodium hydrosulphite solution. The treatment of crude valsartan with Sodium hydrosulfite or hydrose successfully eliminates these impurities to below detection limit.

Accordingly, the present invention provides a process for the preparation of Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino)butanoic acid (NMBA) impurities comprising the steps of;

a) Treating crude Valsartan dissolved in an organic solvent with aqueous sodium hydrosulphite solution;

b) Separating the organic layer obtained from step (a) followed by treatment with water and Sodium chloride solution sequentially;

c) Distilling out the organic solvent completely followed by dissolving residue in methanol followed by treating with alcoholic sodium hydroxide solution, and distilling out methanol completely;

d) Dissolving residue obtained from step (c) in mixture of methanol and ethyl acetate, cooled to effect precipitating of sodium salt of Valsartan;

e) acidifying the sodium salt of Valsartan solution obtained in step (d) with conc. HCl followed by extracting Valsartan into ethyl acetate; and f) Treating the ethyl acetate solution with activated charcoal, followed by cooling the filtrate to isolate the pure Valsartan.

Sodium dithionite commonly known as Sodium hydrosulfite or hydrose plays an important role in complete removal of these toxic impurities.

DETAILED DESCRIPTION OF THE PRESENT INVENTION

The invention will now be described in detail in connection with certain preferred and optional embodiments, so that various aspects thereof may be more fully understood and appreciated.

The present invention provides a process for the preparation of Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino)butanoic acid (NMBA) impurities which process comprises; treating the crude valsartan with sodium hydrosulphite solution to eliminate these impurities to below detection limit and isolating pure valsartan.

The treatment of crude valsartan with Sodium hydrosulfite or hydrose according to the present invention successfully eliminates these impurities to below quantification limit.

The valsartan produced by the process of the present invention meets the requirement of both health agencies i.e. USFDA and EMEA.

Accordingly, the present invention provides a process for the preparation of Valsartan which is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl(nitroso)amino) butanoic acid (NMBA) impurities which process comprising the steps of;

a) Treating crude Valsartan dissolved in an organic solvent with aqueous sodium hydrosulphite solution;

b) Separating the organic layer obtained from step (a) followed by treatment with water and Sodium chloride solution sequentially;

c) Distilling out the organic solvent completely followed by dissolving residue in methanol and treating with alcoholic sodium hydroxide solution; distilling out methanol completely;

d) Dissolving residue obtained from step (c) in mixture of methanol and ethyl acetate, cooled to effect precipitating of sodium salt of Valsartan;

e) acidifying the sodium salt of Valsartan solution obtained in step (d) with conc. HCl followed by extracting Valsartan into ethyl acetate; and f) Treating the ethyl acetate solution with activated charcoal, followed by cooling the filtrate to isolate the pure Valsartan.

The organic solvent according to the process of step a) is a solvent that can solubilize the crude valsartan that may be selected from hydrocarbon solvents, halogenated hydrocarbon solvents, ester solvents, etc.

In one embodiment, the solvent is halogenated hydrocarbon solvent selected from methylene dichloride, ethylene dichloride, chloroform.

In another embodiment, the solvent is an ester solvent selected from ethyl acetate, Propyl Acetate and isobutyl acetate.

The cooling temperature of the process steps d) and f) to affect the precipitation of Valsartan or its salt is in the range of 10 to −10° C.

In a preferred embodiment, the present invention provides a process for the preparation of Valsartan which is substantially free from N-nitrosodimethyl amine (NDMA) and N-nitrosodiethyl amine (NDEA) impurities which process comprising the steps of;

a) Treating crude Valsartan dissolved in an organic solvent with aqueous sodium hydrosulphite solution;

b) Separating the organic layer obtained from step (a) followed by treatment with water and Sodium chloride solution sequentially;

c) Distilling out the organic solvent completely followed by dissolving residue in methanol and treating with alcoholic sodium hydroxide solution; distilling out methanol completely;

d) Dissolving residue obtained from step (c) in mixture of methanol and ethyl acetate, cooled to effect precipitating of sodium salt of Valsartan;

e) acidifying the sodium salt of Valsartan solution obtained in step (d) with conc. HCl followed by extracting Valsartan into ethyl acetate; and f) Treating the ethyl acetate solution with activated charcoal, followed by cooling the filtrate to isolate the pure Valsartan.

In yet another embodiment, the invention provides a process for the preparation of disodium salt of Valsartan which is substantially free from N-nitrosodimethyl amine (MDMA), N-nitrosodiethyl amine (NDEA), N-nitrosodiisopropyl amine (NDIPA), N-nitroso ethyl isopropyl amine (NEIPA), N-nitroso dibutyl amine (NDBA) and 4-(methyl (nitroso)amino)butanoic acid (NMBA) impurities, which comprises the steps of;

(a) Treating crude Valsartan dissolved in an organic solvent with aqueous sodium hydrosulphite solution;

(b) Separating the organic layer obtained from step (a) followed by treatment with water and Sodium chloride solution sequentially;

(c) Distilling out the organic solvent completely followed by dissolving residue in methanol and treating with alcoholic sodium hydroxide solution, distilling out methanol completely; and (d) Dissolving residue obtained from step (c) in mixture of methanol and ethyl acetate, cooled to effect precipitating of disodium salt of Valsartan.

The organic solvent used to dissolve crude valsartan while treating with aqueous sodium hydrosulphite solution is selected from hydrocarbon solvents, halogenated hydrocarbon solvents, ester solvents, etc.

The process for the preparation of highly pure Valsartan is depicted in the Scheme-2 below.

Scheme 2

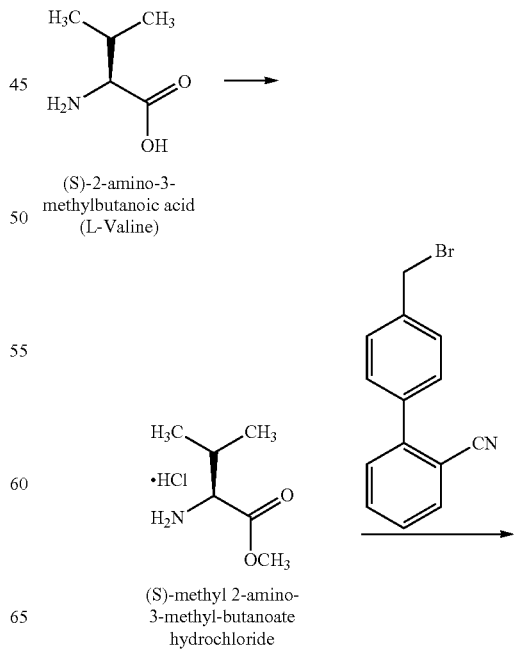

(S)-2-amino-3-methylbutanoic acid (L-Valine)

(S)-methyl 2-amino-3-methyl-butanoate hydrochloride

7
-continued

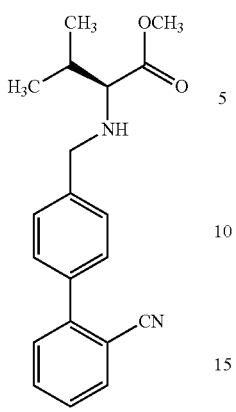

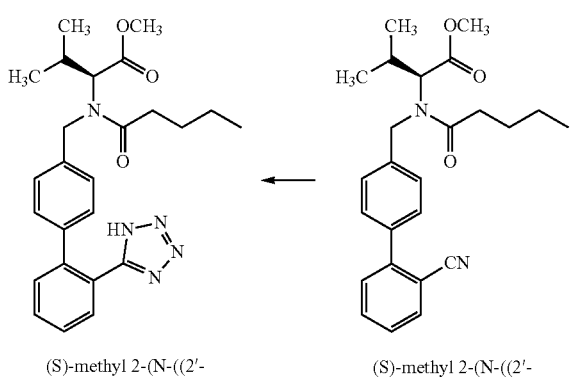

(S)-methyl 2-(N-((2'-(1H-tetrazol-5-yl)-[1,1'-biphenyl]-4-yl)methyl)pentanamido)-3-methylbutanoate (S)-methyl 2-(N-((2'-cyano-[1,1'-biphenyl]-4-yl)methyl)pentanamido)-3-methylbutanoate

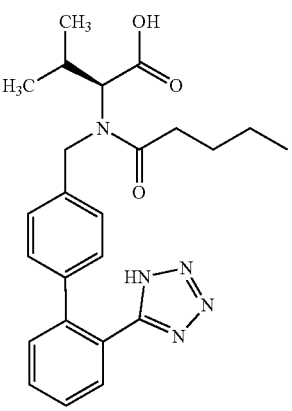

VALSARTAN (Crude)

8
-continued

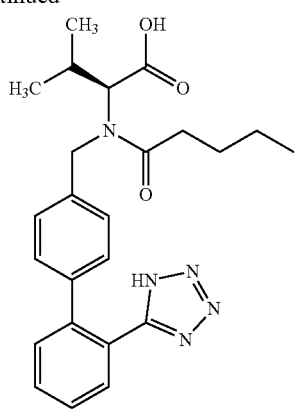

VALSARTAN (Pure)

The inventiveness of the present invention lies in the treatment of crude valsartan having these toxic nitroso amine impurities with sodium hydrosulphite solution.

The aforementioned toxic nitroso amine impurities when treated with sodium hydrosulphite solution gets reduced into corresponding hydrazine, as shown in Scheme 3 and Scheme 4 which goes into the aqueous medium and thus easily removed by water work up process to obtain highly pure Valsartan which is substantially free from toxic nitroso amine impurities.

Scheme 3

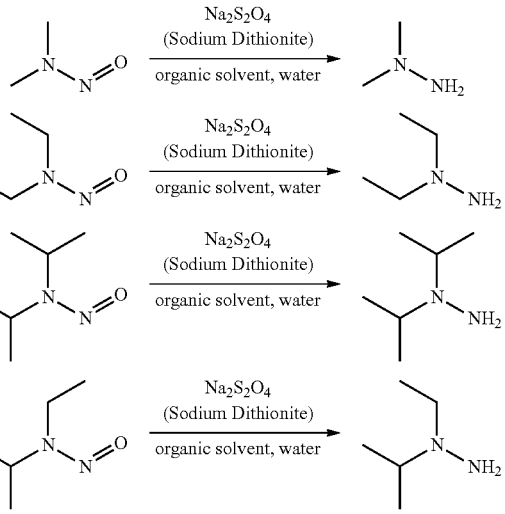

Scheme 4

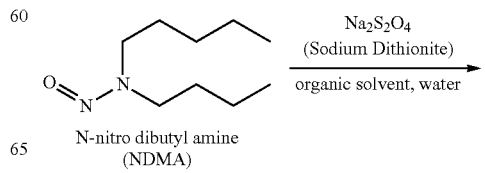

N-nitro dibutyl amine (NDMA)

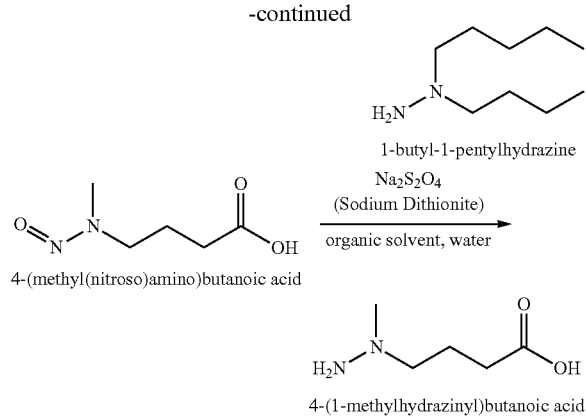

The following examples, which include preferred embodiments, will serve to illustrate the practice of this invention, it being understood that the particulars shown are by way of example and for purpose of illustrative discussion of preferred embodiments of the invention.

EXAMPLES

Example-1:

Crude Valsartan (10 gm) is dissolved in Dichloromethane (150 ml) and charged aqueous solution of sodium hydrosulfite (80 ml). Stirred the reaction mass for 30 min. separated the layers and Dichloromethane layer containing was washed twice with aqueous sodium hydrosulphite solution. Further, the Dichloromethane layer is washed with water and sodium chloride solution respectively. Collected Dichloromethane layer and distilled off Dichloromethane completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 0.49 ppm | 0.04 ppm |
| NDEA | 0.41 ppm | 0.03 ppm |

Example-2:

Crude Valsartan (10 gm) is dissolved in Ethyl acetate (150 ml) and charged aqueous solution of sodium hydrosulfite (80 ml). Stirred the reaction mass for 30 min. separated the layers and Ethyl acetate layer containing was washed twice with aqueous sodium hydrosulphite solution. Further, the Ethyl acetate layer is washed with water and sodium chloride solution respectively. Collected Ethyl acetate layer and distilled off completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 0.49 ppm | 0.03 ppm |
| NDEA | 0.41 ppm | 0.04 ppm |

Example-3:

Crude Valsartan (10 gm) is dissolved in Dichloromethane (150 ml) and charged aqueous solution of sodium hydrosulfite (80 ml). Stirred the reaction mass for 30 min. separated the layers and Dichloromethane layer containing was washed twice with aqueous sodium hydrosulphite solution. Further, the Dichloromethane layer is washed with water and sodium chloride solution respectively. Collected Dichloromethane layer and distilled off completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 1.0 ppm | 0.03 ppm |
| NDEA | 0.8 ppm | 0.07 ppm |

Example-4:

Crude Valsartan (10 gm) is dissolved in Ethyl acetate (150 ml) and charged aqueous solution of sodium hydrosulfite (80 ml). Stirred the reaction mass for 30 min. separated the layers and Ethyl acetate layer containing was washed twice with aqueous sodium hydrosulphite solution. Further, the Ethyl acetate layer is washed with water and sodium chloride solution respectively. Collected Ethyl acetate layer and distilled off completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 1.0 ppm | 0.05 ppm |
| NDEA | 0.8 ppm | 0.04 ppm |

Example-5:

Crude Valsartan (10 gm) is dissolved in Dichloromethane (150 ml) and charged aqueous solution of sodium hydrosulfite (80 ml). Stirred the reaction mass for 30 min. separated the layers and Dichloromethane layer containing was washed twice with aqueous sodium hydrosulphite solution. Further, the Dichloromethane layer is washed with water and sodium chloride solution respectively. Collected Dichloromethane layer and distilled off completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 5.1 ppm | 0.26 ppm |
| NDEA | 4.5 ppm | 0.18 ppm |

Example-6:

Crude Valsartan (10 gm) is dissolved in Ethyl acetate (150 ml) and charged aqueous solution of sodium hydrosulfite (80 ml). Stirred the reaction mass for 30 min. separated the layers and Ethyl acetate layer containing was washed twice with aqueous sodium hydrosulphite solution. Further, the Ethyl acetate layer is washed with water and sodium chloride solution respectively. Collected Ethyl acetate layer and distilled off completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain Disodium Valsartan. This sodium salt was dissolved in water and acidified with conc. HCl up to pH 2.5 to 3.5. The product is extracted in ethyl acetate and washed ethyl acetate layer with Sodium Chloride solution. Distilled out Ethyl acetate completely and residue obtained was dissolved again in Ethyl acetate followed by charcoalization. Collected the filtrate after charcoalization and cooled to 0° C. The white solid was precipitate out, filtered and dried under vacuum to get pure Valsartan having nitrosoamine impurities are well below the limit of quantification.

| Impurity | Initial | After purification using Sodium Hydrosulfite |
|---|---|---|
| NDMA | 5.0 ppm | 0.11 ppm |
| NDEA | 5.0 ppm | 0.13 ppm |

Example-7:

Crude Valsartan (10 gm) is dissolved in Ethyl acetate (150 ml) and charged aqueous solution of sodium hydrosulfite (80 ml). Stirred the reaction mass for 30 min. Separated the layers and Ethyl acetate layer containing main product was washed twice with aqueous sodium hydrosulphite solution. Further, the Ethyl acetate layer is washed with water and sodium chloride solution respectively. Collected Ethyl acetate layer and distilled off Ethyl acetate completely. The residue obtained was dissolved in Methanol. To this reaction mass methanolic NaOH solution was added and methanol is distilled off completely. The residue obtained is dissolved in a mixture of Methanol and Ethyl acetate. Cooled to 0° C. and white solid was precipitated out. Filtered and dried to obtain disodium salt of Valsartan (8.5 gm) having nitrosoamine impurities well below the limit of quantification.

Method of Analysis of Pure Valsartan and Disodium Salt of Valsartan by HPLC

Chromatographic Conditions:

| Instrument | HPLC (Make-ThermoUltima 3000) equipped with UV detector or equivalent. |
|---|---|
| HPLC System | Gradient |
| Mobile phase-A | Buffer |
| Mobile phase-B | Acetonitrile |
| Mobile phase-C | Methanol |
| Column | YMC-Pack Pro C18/S-5 µm/12 nm; 250 mm × 4.6 mm × 5µ or Equivalent |
| Wavelength | 225 nm |
| Flow rate | 1.0 ml/min. |
| Column Oven | 40° C. |
| Injection Volume | 300 µL |
| Autosampler temp. | 10° C. |
| Run time | 60.0 min. |
| Diluent | Only Buffer solution. |

We claim:
1. A process for the purification of Valsartan, comprising:
    a) dissolving crude valsartan in an organic solvent to form a valsartan solution;
    b) treating the valsartan solution with a sodium hydrosulphite solution; and
    c) isolating substantially pure valsartan from the treated valsartan solution,
        wherein the substantially pure valsartan is substantially free from nitrosamine impurities.
2. The process of claim 1, wherein the substantially pure valsartan is substantially free from N-nitrosodimethyl amine (NDMA), N-nitrosodiethyl amine (NDEA) and N-nitrosodiisopropyl amine (NDIPA) N-nitroso ethyl isopropyl amine (NEIPA), N-nitroso dibutyl amine (NDBA) and 4-(methyl (nitroso) amino) butanoic acid (NMBA).
3. The process of claim 1, wherein:
    the substantially pure valsartan contains N-nitrosodimethyl amine (NDMA) in a concentration of 0.26 ppm or less; and
    the substantially pure valsartan contains N-nitrosodiethyl amine (NDEA) in a concentration of 0.18 ppm or less.
4. The process of claim 1, wherein the step of treating the valsartan solution with the sodium hydrosulphite solution reduces a concentration of the nitrosamine impurities to below a detection limit.
5. A process for the purification of Valsartan, comprising;
    (a) dissolving crude valsartan in an organic solvent to form a valsartan solution;
    (b) treating the valsartan solution with an aqueous sodium hydrosulphite solution to obtain an organic layer and an aqueous layer;
    (c) separating the organic layer from the aqueous layer, and treating the organic layer sequentially with water and sodium chloride solution;
    (d) evaporating the organic solvent from the organic layer to obtain a first residue, followed by dissolving the first residue in methanol to obtain a first residue solution, and treating the first residue solution with alcoholic sodium hydroxide solution, and evaporating methanol from the residue solution to obtain a second residue;
    (e) dissolving the second residue in a mixture of methanol and ethyl acetate to obtain a second residue solution, and cooling the second residue solution to precipitate a disodium salt of Valsartan; and
    f) converting the disodium salt of Valsartan into substantially pure Valsartan, wherein the substantially pure valsartan is substantially free from nitrosamine impurities.
6. The process of claim 5, wherein the step of converting the disodium salt of Valsartan into substantially pure Valsartan comprises:
    reacting the disodium salt of Valsartan with concentrated HCl to obtain valsartan, and precipitating the valsartan from ethyl acetate.
7. The process of claim 6, wherein the step of precipitating the valsartan from ethyl acetate comprises:
    dissolving the valsartan in ethyl acetate to obtain an ethyl acetate solution,
    treating the ethyl acetate solution with activated charcoal, followed by filtration to obtain a filtrate; and
    cooling the filtrate to precipitate the valsartan.
8. The process as claimed in claim 1, wherein the step of dissolving the crude valsartan in the organic solvent comprises dissolving the crude valsartan in a hydrocarbon solvent, a halogenated hydrocarbon solvent, an ester solvent, or a mixture thereof.
9. The process as claimed in claim 5, wherein the step of dissolving the crude valsartan in the organic solvent comprises dissolving the crude valsartan in a hydrocarbon solvent, a halogenated hydrocarbon solvent, an ester solvent, or a mixture thereof.
10. The process as claimed in claim 8, wherein the step of dissolving the crude valsartan in the organic solvent comprises dissolving the crude valsartan in the halogenated hydrocarbon solvent, wherein the halogenated hydrocarbon solvent is methylene dichloride, ethylene dichloride, chloroform, or a mixture thereof.
11. The process as claimed in claim 9, wherein the step of dissolving the crude valsartan in the organic solvent comprises dissolving the crude valsartan in the halogenated hydrocarbon solvent, wherein the halogenated hydrocarbon solvent is methylene dichloride, ethylene dichloride, chloroform, or a mixture thereof.
12. The process as claimed in claim 8, wherein the step of dissolving the crude valsartan in the organic solvent comprises dissolving the crude valsartan in the ester solvent, wherein the ester solvent is ethyl acetate, propyl acetate, isobutyl acetate, or a mixture thereof.
13. The process as claimed in claim 9, wherein the step of dissolving the crude valsartan in the organic solvent comprises dissolving the crude valsartan in the ester solvent, wherein the ester solvent is ethyl acetate, propyl acetate, isobutyl acetate, or a mixture thereof.
14. The process as claimed in claim 5, wherein the step of cooling the second residue solution to precipitate the disodium salt of Valsartan comprises cooling the second residue solution to a temperature of −10° C. to +10° C.
15. The process as claimed in claim 6, wherein the step of precipitating the valsartan from ethyl acetate comprises dissolving the valsartan in ethyl acetate to obtain an ethyl acetate solution, and cooling the ethyl acetate solution to a temperature of −10° C. to +10° C.
16. A process for preparing a disodium salt of Valsartan, comprising;
    (a) dissolving crude valsartan in an organic solvent to form a valsartan solution;
    (b) treating the valsartan solution with an aqueous sodium hydrosulphite solution to obtain an organic layer and an aqueous layer;
    (c) separating the organic layer from the aqueous layer, and treating the organic layer sequentially with water and sodium chloride solution;
    (d) evaporating the organic solvent from the organic layer to obtain a first residue, followed by dissolving the first residue in methanol to obtain a first residue solution, and treating the first residue solution with alcoholic sodium hydroxide solution, and evaporating methanol from the residue solution to obtain a second residue;
    (e) dissolving the second residue in a mixture of methanol and ethyl acetate to obtain a second residue solution, and cooling the second residue solution to precipitate a disodium salt of Valsartan,
        wherein the disodium salt of Valsartan is substantially free from nitrosamine impurities.
17. The process as claimed in claim 16, wherein the step of dissolving the crude valsartan in the organic solvent comprises dissolving the crude valsartan in a hydrocarbon solvent, a halogenated hydrocarbon solvent, an ester solvent, or a mixture thereof.
18. The process as claimed in claim 17, wherein the step of dissolving the crude valsartan in the organic solvent comprises dissolving the crude valsartan in the halogenated hydrocarbon solvent, wherein the halogenated hydrocarbon solvent is methylene dichloride, ethylene dichloride, chloroform, or a mixture thereof.

19. The process as claimed in claim 17, wherein the step of dissolving the crude valsartan in the organic solvent comprises dissolving the crude valsartan in the ester solvent, wherein the ester solvent is ethyl acetate, propyl acetate, isobutyl acetate, or a mixture thereof.

* * * * *